(12) United States Patent
Linnenkohl et al.

(10) Patent No.: US 8,538,125 B2
(45) Date of Patent: Sep. 17, 2013

(54) METHOD FOR RECOGNIZING A STRUCTURE TO BE APPLIED TO A SUBSTRATE, WITH THE AID OF SEVERAL CAMERAS AND DEVICE THEREFORE

(75) Inventors: Jan Anders Linnenkohl, Bensheim (DE); Andreas Tomtschko, Weinsberg (DE); Mirko Berger, München (DE); Roman Raab, München (DE)

(73) Assignee: Quiss GmbH, Puchheim (DE)

( * ) Notice: Subject to any disclaimer, the term of this patent is extended or adjusted under 35 U.S.C. 154(b) by 1824 days.

(21) Appl. No.: 10/584,196

(22) PCT Filed: Dec. 23, 2004

(86) PCT No.: PCT/EP2004/014698
§ 371 (c)(1),
(2), (4) Date: Jun. 29, 2007

(87) PCT Pub. No.: WO2005/063406
PCT Pub. Date: Jul. 14, 2005

(65) Prior Publication Data
US 2012/0039524 A1    Feb. 16, 2012

(30) Foreign Application Priority Data
Dec. 23, 2003  (DE) .................................. 103 61 018

(51) Int. Cl.
*G06K 9/00*    (2006.01)
(52) U.S. Cl.
USPC ............ 382/141; 382/153; 348/143; 700/259

(58) Field of Classification Search
USPC ................. 382/103, 141, 153; 348/125, 143, 348/169; 700/259
See application file for complete search history.

(56) References Cited

U.S. PATENT DOCUMENTS

| | | | |
|---|---|---|---|
| 3,742,901 A | | 7/1973 | Johnston |
| 4,380,696 A | * | 4/1983 | Masaki .................... 219/124.34 |
| 4,568,816 A | * | 2/1986 | Casler, Jr. ................ 219/124.34 |
| 4,575,304 A | * | 3/1986 | Nakagawa et al. ........... 414/730 |
| 4,576,482 A | | 3/1986 | Pryor |
| 4,616,121 A | * | 10/1986 | Clocksin et al. ......... 219/124.34 |
| 4,628,464 A | | 12/1986 | McConnell |

(Continued)

FOREIGN PATENT DOCUMENTS

| | | |
|---|---|---|
| DE | 3243341 A1 | 6/1983 |
| DE | 3506110 A1 | 9/1986 |

(Continued)

OTHER PUBLICATIONS

PCT International Search Report Dated Nov. 25, 2005, Appliant Quiss GmbH et al., Application No. PCT/EP2004/014698, 15 Pages.

(Continued)

*Primary Examiner* — Aaron W Carter
(74) *Attorney, Agent, or Firm* — Brooks Kushman P.C.

(57) ABSTRACT

A method and apparatus are provided for automatic application and monitoring of a structure to be applied onto substrate. A plurality of cameras positioned around an application facility are utilized to monitor the automatic application of a structure on a substrate by means of a stereometry procedure. Three-dimensional recognition of a reference contour position results in the overlapping area to be used for gross adjustment of the application facility prior to applying the structure.

28 Claims, 9 Drawing Sheets

(56) References Cited

U.S. PATENT DOCUMENTS

| | | | |
|---|---|---|---|
| 4,666,732 A | 5/1987 | Schucker | |
| 4,724,302 A | 2/1988 | Penney et al. | |
| 4,843,287 A * | 6/1989 | Taft | 318/568.16 |
| 4,849,679 A | 7/1989 | Taft et al. | |
| 4,907,169 A * | 3/1990 | Lovoi | 700/259 |
| 4,916,286 A | 4/1990 | Sarugaku et al. | |
| 4,965,499 A * | 10/1990 | Taft et al. | 318/568.11 |
| 4,969,199 A | 11/1990 | Nara | |
| 4,998,502 A | 3/1991 | Schucker | |
| 5,006,999 A * | 4/1991 | Kuno et al. | 700/253 |
| 5,110,615 A | 5/1992 | Maiorca et al. | |
| 5,402,351 A * | 3/1995 | Batchelder et al. | 700/119 |
| 5,429,682 A | 7/1995 | Harlow, Jr. et al. | |
| 5,510,149 A | 4/1996 | Schucker | |
| 5,517,419 A * | 5/1996 | Lanckton et al. | 701/409 |
| 5,532,452 A | 7/1996 | Lechner et al. | |
| 5,533,146 A | 7/1996 | Iwai | |
| 5,572,102 A * | 11/1996 | Goodfellow et al. | 318/568.13 |
| 5,572,103 A * | 11/1996 | Terada | 318/568.13 |
| 5,807,449 A * | 9/1998 | Hooker et al. | 156/64 |
| 5,878,151 A | 3/1999 | Tang et al. | |
| 5,932,062 A | 8/1999 | Manser | |
| 5,937,143 A * | 8/1999 | Watanabe et al. | 700/264 |
| 5,959,425 A * | 9/1999 | Bieman et al. | 318/568.15 |
| 6,064,429 A | 5/2000 | Belk et al. | |
| 6,064,759 A | 5/2000 | Buckley et al. | |
| 6,356,299 B1 | 3/2002 | Trosino et al. | |
| 6,541,757 B2 * | 4/2003 | Bieman et al. | 250/221 |
| 6,763,284 B2 * | 7/2004 | Watanabe et al. | 700/264 |
| 7,112,246 B2 | 9/2006 | Schucker | |
| 7,177,459 B1 | 2/2007 | Watanabe et al. | |
| 7,577,285 B2 | 8/2009 | Schwarz et al. | |
| 7,945,349 B2 * | 5/2011 | Svensson et al. | 700/254 |
| 8,116,928 B2 * | 2/2012 | Wu et al. | 701/23 |
| 8,137,738 B2 * | 3/2012 | Linnenkohl et al. | 427/8 |
| 2002/0084260 A1 * | 7/2002 | Kubota et al. | 219/121.63 |
| 2003/0043116 A1 | 3/2003 | Morrison et al. | |
| 2003/0078694 A1 * | 4/2003 | Watanabe et al. | 700/245 |
| 2004/0011284 A1 * | 1/2004 | Schucker | 118/688 |
| 2005/0027399 A1 * | 2/2005 | Koh et al. | 700/258 |
| 2005/0251290 A1 * | 11/2005 | Skourup et al. | 700/245 |
| 2005/0259245 A1 | 11/2005 | Cemic et al. | |
| 2006/0147103 A1 * | 7/2006 | Linnenkohl et al. | 382/141 |
| 2007/0292629 A1 * | 12/2007 | Linnenkohl et al. | 427/466 |
| 2008/0024602 A1 | 1/2008 | Linnenkohl et al. | |
| 2010/0042319 A1 * | 2/2010 | Wu et al. | 701/207 |
| 2010/0152944 A1 * | 6/2010 | Kouno et al. | 701/26 |
| 2011/0106311 A1 * | 5/2011 | Nakajima et al. | 700/253 |
| 2011/0282492 A1 * | 11/2011 | Krause et al. | 700/259 |
| 2012/0039524 A1 * | 2/2012 | Linnenkohl et al. | 382/145 |

FOREIGN PATENT DOCUMENTS

| | | |
|---|---|---|
| DE | 268049 A1 | 5/1987 |
| DE | 69103951 T3 | 10/1997 |
| DE | 69410684 T2 | 12/1998 |
| DE | 19852079 A1 | 5/2000 |
| DE | 10048749 A1 | 4/2002 |
| EP | 0203803 A1 | 12/1986 |
| EP | 0576498 A1 | 1/1994 |
| FR | 2741438 A1 | 5/1997 |
| FR | 2817618 A1 | 6/2002 |
| JP | 2277573 A | 11/1990 |
| WO | 0226397 A1 | 4/2002 |
| WO | 2005065844 A1 | 7/2005 |

OTHER PUBLICATIONS

Office Action Dated Apr. 24, 2012, U.S. Appl. No. 10/584,120.
Amendment Under 37 C.F.R. 1.111 Dated Aug. 24, 2012, U.S. Appl. No. 10/584,120.
Notice of Allowance Dated Dec. 12, 2012, U.S. Appl. No. 10/584,120, Inventor—Jan Anders Linnenkohl et al., 4 Pages.

* cited by examiner

METHOD FOR RECOGNIZING A STRUCTURE TO BE APPLIED TO A SUBSTRATE, WITH THE AID OF SEVERAL CAMERAS AND DEVICE THEREFORE

The present application relates to and claims priority from International Application Serial No. PCT/EP2004/014698 filed Dec. 23, 2004, titled "METHOD FOR RECOGNISING A STRUCTURE TO BE APPLIED TO A SUBSTRATE, WITH THE AID OF SEVERAL CAMERAS AND DEVICE THEREFOR", which claims priority to German Application No. 10361018.9 filed Dec. 23, 2003, the complete disclosures of which are hereby expressly incorporated in their entirety.

The present invention relates to a method for recognizing a structure to be applied onto a substrate with at least one or more cameras, and a corresponding apparatus.

For recognizing a structure to be applied onto a substrate it has been customary to carry out optical measurements. Frequently various systems for fully automatic testing of the structure, including adhesive and sealing agent lines, are used. For this purpose, multiple video cameras are directed at the structure to be recognized. In addition, an illumination module serving to generate a contrast-rich camera image is required.

In order to be able to monitor an adhesive line or adhesive trail while the structure is being applied, it is necessary to teach-in a reference adhesive trail (i.e., to have the camera or cameras scan the reference adhesive tail) in order to calculate corresponding parameters on which the assessment of the applied adhesive trails are subsequently based.

Conventionally there was a necessity in the teaching-in of a reference adhesive trail for each camera to individually scan the adhesive trail in order to obtain camera images for all positions. When using three cameras, the reference adhesive trail had to be scanned thrice in sequence and the three different sequences of images of the three cameras had to be assigned. A disadvantage with this method is that the parameterization of the reference adhesive trail being cumbersome and time consuming and can lead to high inaccuracy.

Moreover, there is a need for a method to recognize a structure to be applied onto a substrate using at least one or more cameras, and to monitor an application structure or adhesive trail at a high accuracy and speed while the structure is being applied.

It is therefore the present invention is to provide a method for recognizing a structure to be applied onto a substrate for at least one or more cameras. The method facilitates rapid start-up at a high accuracy and permits quick teach-in of the reference adhesive trail.

Moreover, an object of the present invention is to provide a method for recognizing a structure to be applied onto a substrate using at least one or more cameras. The method monitors an application structure or adhesive trail at a high accuracy and speed while the structure is being applied.

Moreover, an object of the present invention is to provide a suitable apparatus for carrying out the method according to the invention.

In the method and apparatus according to the invention, a reference application structure is taught-in. In addition, further applied application structures or adhesive trails are compared to the reference application structure for assessment. The application facility according to the invention (i.e., the application facility with cameras or as a kinematic inversion) can be moved or the substrate can be moved.

The method facilitates by means of teaching-in a reference application structure, and recording and storing of the images of all cameras in a sequence of images. The cameras take a single scan of said reference application structure. The single scan reduces the time of the start-up of an apparatus because of a short teach-in time.

According to a method of the invention for recognizing a structure to be applied onto a substrate, (e.g., preferably an adhesive line or adhesive trail) at least one camera, (e.g., in particular multiple cameras), is used during the scanning for assessment of the structure and is processed in the form of an optical representation. Each camera records a strip of the image to form a sequence of images, and the image recording rate is increased in line with the data reduction achieved by recording only a strip of the image. An advantage is that the method is highly accurate and can be fully automated. This allows the adhesive trail to be monitored in parallel or simultaneous to the application of the adhesive trail.

Furthermore, an advantage is for each camera to record a strip of the image to form a part of a sequence of images to minimize the data to be included in a calculation. Because less data is included in the calculation and because of the high image recording rate, recording small partial sections of the whole adhesive trail to be recorded (e.g., between 1 mm and 3 mm) is feasible. The adhesive trail being a type of vector chain can be followed automatically in the individual images.

Moreover, another advantage is to increase the image recording rate in line with the data reduction achieved by recording only a strip of the image. In particular by using the partial scanning technique, a higher frame rate is attained. Thus, capturing images synchronously and in parallel by all cameras at the same time is feasible. The image recording therefore proceeds at defined fixed time intervals and is independent of robot control.

According to the invention, the image strips of the individual cameras are joined to form a single image. Thus, the respective images of the individual cameras are assigned accordingly independent of location and can be recorded and processed synchronously. In addition, errors are prevented in the teach-in because the images of the individual cameras are always assigned with a correct time and a location.

According to a preferred embodiment, each camera uses only approximately a quarter of the image lines as image strips, thus quadrupling the image recording rate. Moreover, an advantage of the parameterization of the sequence of images obtained from the reference application structure is that the results from a single image recording run of all cameras is automatically performed by means of a one-time external indication or external marking (e.g. by means of a mouse click) of the reference application structure. The external marking is used for comparison to an applied adhesive trail. In particular, the robot travel path, the robot travel time, the direction, the width and the quality of the adhesive trail are used for parameterization. This simple parameterization procedure reduces the risk of maloperation or incorrect parameterization. The system can be also be operated by personnel with low qualifications. Thus, the parameterization generates a vectorization of the entire adhesive trail. The vectorization provides for reliable and automatic monitoring of the adhesive trail because of the high image recording rate. In addition, the vectorization results in a switch of the sensor head requiring recalibration or new calibration without having to teach-in again the adhesive trail.

According to a preferred embodiment of the invention, an assessment function, in particular a fuzzy assessment is used to analyze the adhesive agent track or adhesive trail. In particular the width of the pair of edges comprising the right and the left edge of the adhesive trail, the mean gray scale value of the projected gray scale value profile between the pair of edges, the edge contrast, and the progression of position are included in the calculation by means of the assessment function. As a result, the adhesive trail can be described accurately such that the adhesive trail can be recognized automatically in a reliable fashion.

Moreover, an advantage for the edge of the adhesive trail to be determined on a surrounding track or orbit (e.g., an essentially circular track) or circular line in order to capture any progression of the adhesive trail around the application facility in a defined area. The adhesive trail progresses within the surrounding track, which can be elliptical, polygonal, or approximately circular.

According to a preferred embodiment, the center of the circular line or the surrounding track essentially coincides with the site from which the adhesive emanates to form the adhesive trail. Each camera monitors at least one segment of the circle formed by the circular line.

Errors at the transition from one camera to the next can be reduced by having each camera monitor at least one overlapping area jointly with at least one adjacent camera.

It is particularly advantageous for the angle values of the circular line ranging from 0 to 360° form a global coordinate system of the individual cameras. A segment of the circular line is assigned to the images of the individual cameras. As a result, the progression of the adhesive trail can be followed by at least one active camera, whereby statements concerning the entire adhesive trail as well as the position or progression of the adhesive trail can be made by relatively simple means.

According to a preferred embodiment, a first camera covers a range of angles ranging from −10° to 130°, a second camera covers a range of angles from 110° to 250°, and a third camera covers a range of angles from 230° to 10°, where three cameras are being used.

Moreover, during the progression of the adhesive trail, an advantage is to automatically switch from one camera to the next when the adhesive trail progresses from the segment of a circular line of one camera via the overlapping area to the segment of a circular line of a different camera. As a result, it is feasible to reliably follow the progression of the track or position of the track, and these are predictable accordingly. Therefore, fully automatic switching between neighboring cameras can occur such that the parameterization times are reduced.

Moreover, an advantage of light emitting diode (LED) illumination means is the color that provides a suitable contrast to the color of the application structure is used for illumination. A color of the light is selected such that, according to the principle of complementary colors, a maximal contrast between the substrate and the adhesive trail results. An advantage of the invention is to use infrared LEDs or ultraviolet LEDs (UV LEDs) that emit red, green and blue light, in particular upon the use of red-green-blue LEDs (RGB LEDs). As a consequence of using LEDs, the sensor design can be switched to a corresponding adhesive color without further reconfiguration.

If triple colored LEDs (e.g., red, green, and blue) are used, the most suitable color combined can be generated for optimal contrast.

According to a further development of the invention, the LEDs are flashed, in particular, by utilizing pulses of current (e.g., ranging from 1.0 to 0.01 ms) applied to the diodes. Flashing the diodes, obtains focused images of the adhesive trail, while the sensor scans over the substrate.

Moreover, for three-dimensional positional correction for the application facility is performed by means of the stereometry procedure with regard to positional tolerances of the individual components or tolerances of the joining seams and provides an advantage for the reference contour or a feature to be determined by at least two cameras.

Another advantage is if the two cameras record the substrate, a section of the component, or one or more components in the form of a full image or large image, whereby the full images or large images of the two cameras comprise an overlapping area in a leading direction. The three-dimensional recognition of the reference contour position results in the overlapping area used for gross adjustment of the application facility prior to applying the structure. Thus, corresponding correction values are transmitted to the application facility or the robot in order to shift the application facility's or robot's coordinate system for the application of the adhesive agent.

If a projection is made onto the area of the reference contour for a three-dimensional analysis, (e.g., if one or more laser lines are applied to the substrate in the form of a projection), then the three-dimensional analysis of the profile with regard to the height and contour of arbitrary components can be facilitated even though this is not analyzable by common image processing without an additional projection.

An advantage of the invention is the individual cameras are calibrated in order to assign the angle assignment of the individual cameras according to a circular caliper. In particular a circular arc of the calibrating device with marker points at 0°, 120°, and 240° for three cameras is used. The marker points allow a global coordinate system to be used with regard to the angle assignment for the individual cameras on the circular caliper around the application facility in order to simplify the processing by software.

Moreover, the distance of the application facility from a feature of the component (e.g., from edges of the component, or holes or breakthroughs) can be measured in order to carry out a positional test of the applied structure. A line-shaped gray scale value scan or line-shaped calipers are used for distance measurement such that any number of reference markers can be placed along the circular arc of the calibrating device. Image processing is not exclusively limited to the camera image, in which the adhesive trail test is carried out. It is therefore not necessary for the adhesive trail and suitable reference features to be visualized in the same camera image, which has a particular advantage with regard to the parallel processing of three camera images.

The present invention also provides an apparatus for recognizing a structure to be applied onto a substrate, preferably an adhesive line or adhesive trail, whereby at least one illumination module and one sensor unit are provided. The sensor unit includes at least one or more cameras that are arranged around the facility for applying the structure. Each camera is directed at the facility for applying the structure. By this means the travel path of the facility over a substrate or a travel path of the substrate relative to the application facility to be monitored at all times in all directions by means of directing the cameras at the application facility is feasible.

An advantage is if the axial longitudinal axis of the individual cameras essentially intersects (e.g., in the direction of view or along the axial longitudinal axis of the application facility), a narrow area around the application facility can be monitored at suitable resolution and high image recording rate.

According to a preferred embodiment, individual cameras, in particular 3 cameras, are arranged at equal distances from each other in the direction of the circumference.

The individual cameras are circuited such that the images of the cameras are stored in a sequence of images such that these images can be recorded synchronously and in parallel as well as in an assigned fashion.

According to a development of an invention, one or more cameras form a circular caliper whose center is formed by the application facility of the structure. Thus, one or more circular calipers can be used to facilitate the determination of the edge of the adhesive trail on a circular line.

According to a preferred embodiment, the individual cameras comprise an overlapping area of at least 10° each relative to the adjacent camera. This overlapping area facilitates fully automatic switching between neighboring cameras when the adhesive trail progresses from the monitoring area of one camera to the next. Because the selection of the camera is not bound to the robot position or a time component, but rather always refers to the actual inspection results. For instance, the inspection results are based on the arrangement, the orbit, the circular line of the circular caliper, or the global coordinate system formed thereby.

Moreover, an advantage is for the illumination module to comprise light emitting diodes (LEDs), in particular infrared LEDs, ultra-violet LEDs (UV LEDs) or Red-Green-Blue LEDs (RGB LEDs).

Moreover, an advantage is the use of a calibrating disc with individual form elements for calibrating the individual cameras for the assignment of the angle assignment. The form elements comprise, in particular, an angle distance of essentially 10°, which allows for assignment of a scaling factor, an angle assignment, and a center and a radius of the search circle for the individual cameras. According to the invention, the calibrating disc comprises at least three marker sites that are arranged in a circular arc of the calibrating disc (e.g. essentially located at 0°, 120°, and 240°), in order to calibrate the three cameras.

If a projection facility projecting one or more features (e.g., in particular strips) onto the substrate for the three-dimensional analysis is provided on the application facility, arbitrary components can be used for correction or adjustment of the application facility prior to applying the structure.

According to a preferred embodiment, the projection facility emits one or more laser lines for a three-dimensional profile analysis. Arranging at least two projection facilities around the application facility facilitates a gap-free three-dimensional analysis around the application facility. Means of image processing, whereby the analyses of a sealing agent height and a sealing agent contour, as well as a position and a width, can be performed according to the principle of triangulation.

Advantages of the invention shall be illustrated in an exemplary fashion by means of the following drawings.

Figure 1:
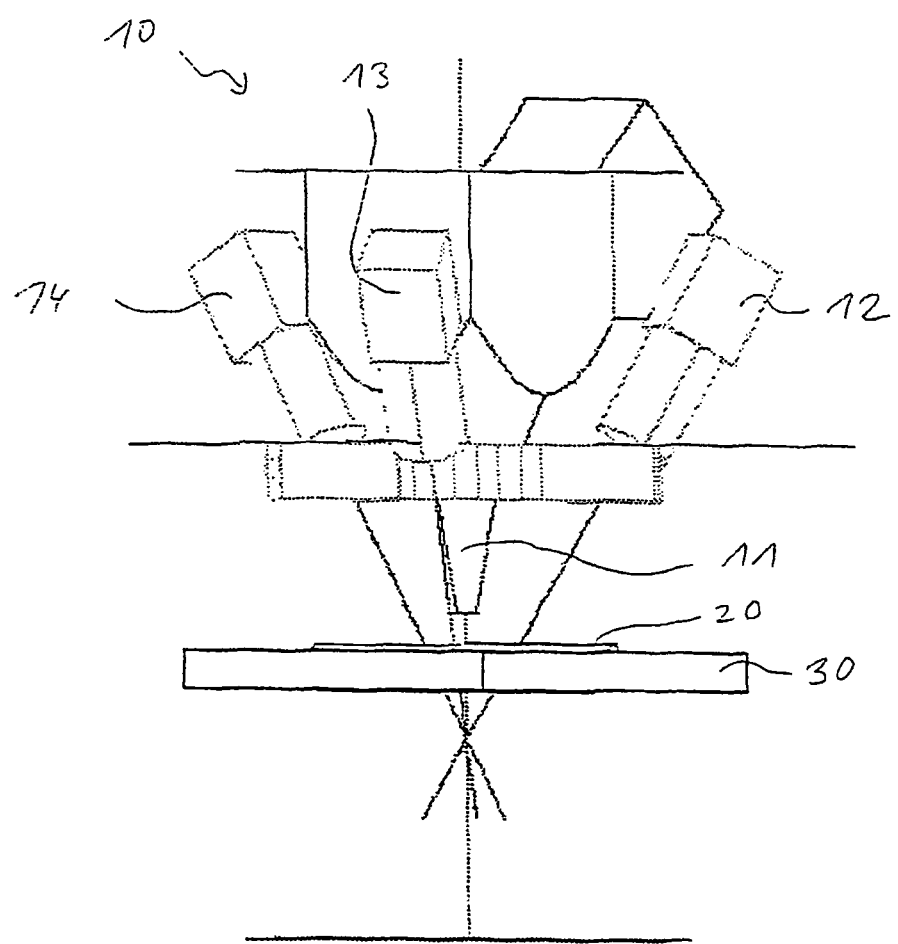
FIG. 1 illustrates a schematic side view of an apparatus according to the invention for application and monitoring of an adhesive trail.

Reference number 10 illustrated in FIG. 1 indicates schematically an apparatus for the application and recognition of an adhesive trail 20. In the center of the apparatus is arranged an application facility 11 by means of which an adhesive trail 20 is applied onto a substrate 30 or onto a sheet of metal 31 proceeding from right to left in FIG. 1. Three cameras 12, 13, 14 are arranged at equal distances from each other in a circle around the application facility 11, wherein each camera is directed at the application facility 11. As is evident from FIG. 1, the axial longitudinal axes of the three cameras 12, 13, 14 intersect the axial longitudinal axis of the application facility 11 below the substrate 30 such that the focus of the individual cameras 12, 13, and 14 are arranged around the area of the application facility 11, in particular, on a circular line.

Figure 2:
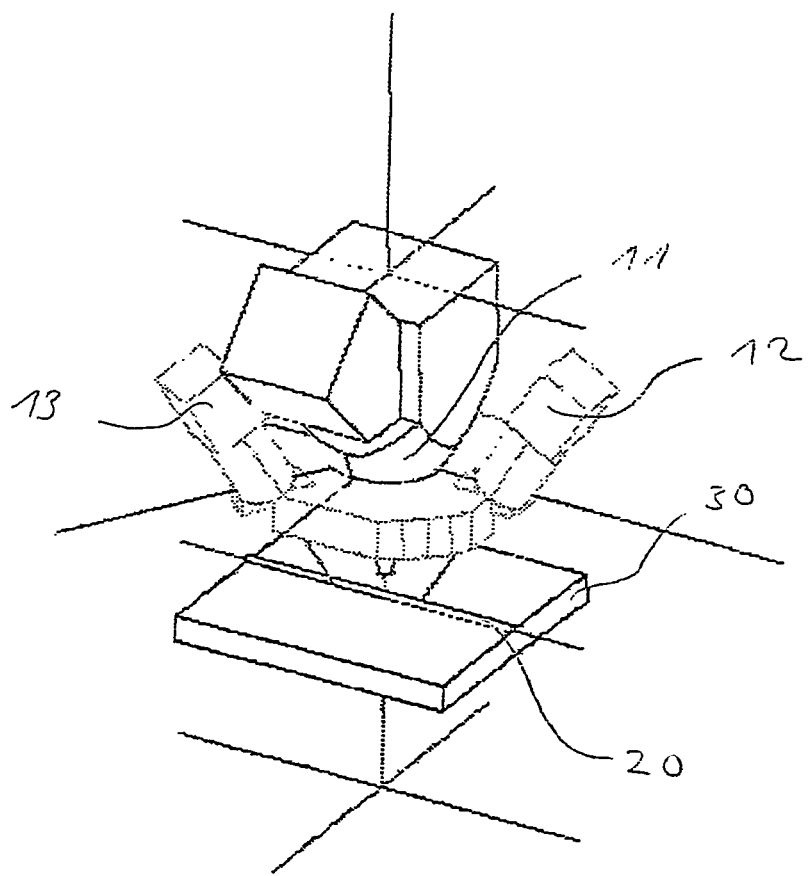
FIG. 2 illustrates a perspective view of an apparatus according to the invention of FIG. 1.

In the inspection of the adhesive, either the application facility 11 with the cameras 12, 13, and 14 or the substrate 30 is moved. The adhesive trail 20 is simultaneously applied to the substrate 30 by means of the application facility 11, whereby the cameras 12, 13, 14 monitor the applied structure. Thus, either the application facility 11 with the cameras 12, 13 and 14 or the substrate 30 can be moved, in order to apply the adhesive trail 20 onto the substrate 30 such as to follow a desired progression. By this means, the moving cameras 12, 13, and 14 can monitor, independent of the path of travel, the adhesive trail 20 at the time the adhesive trail 20 is being applied. In FIG. 2, the adhesive trail 20 progresses from left to right and is indicated by a continuous line. The intended progression of the adhesive trail 20 is indicated by a dashed line to the right of the application facility 11.

Figure 3:
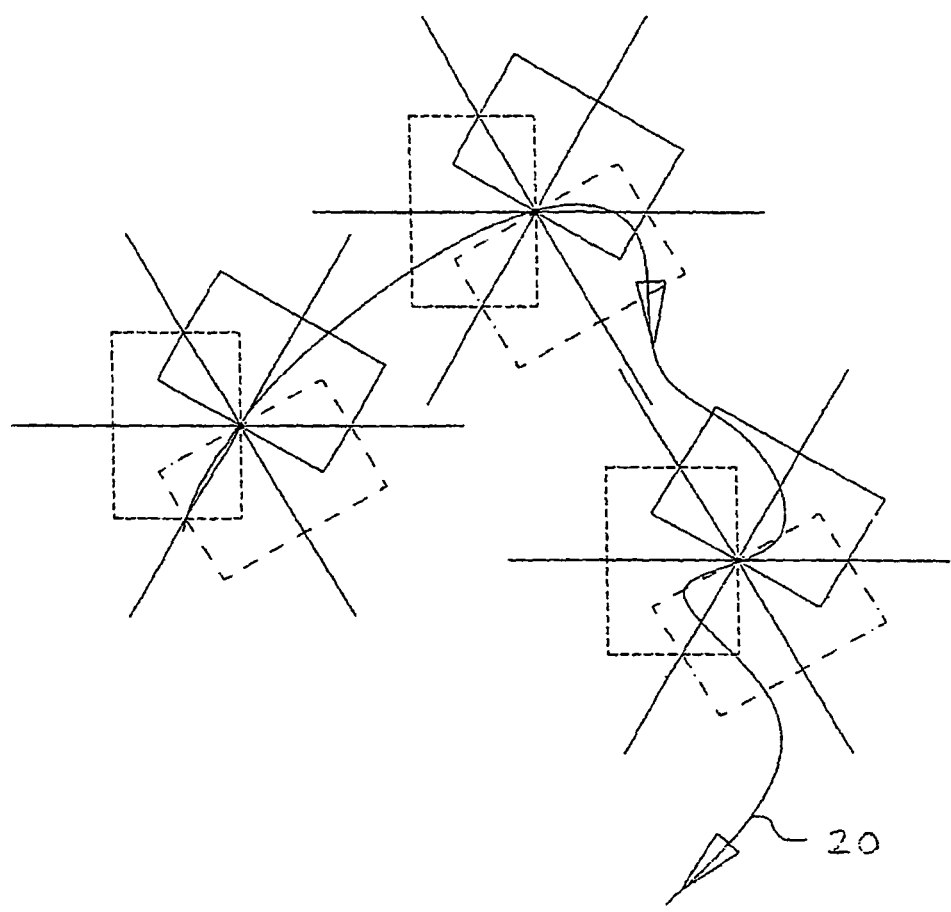
FIG. 3 illustrates a travel path of the apparatus according to the invention for application and monitoring of an adhesive trail.

FIG. 3 illustrates the progression of the adhesive trail 20 as indicated by arrows 21 and 22, whereby the direction or field of view of the three individual cameras 12, 13 and 14 are shown in three sites 23, 24 and 25. The field of view 23, 24, and 25 of the three individual cameras 12, 13 and 14 is indicated by a rectangle drawn with a continuous line 24, a rectangle drawn with widely dashed lines 23, and a rectangle drawn with narrow dashed lines 25. As shown in from FIG. 3, the direction of the individual fields of view 23, 24, and 25 of the cameras 12, 13 and 14 remains constant at all times whereby only the whole apparatus is moved along the adhesive trail 20 as indicated by arrows 21 and 22.

Figure 4:
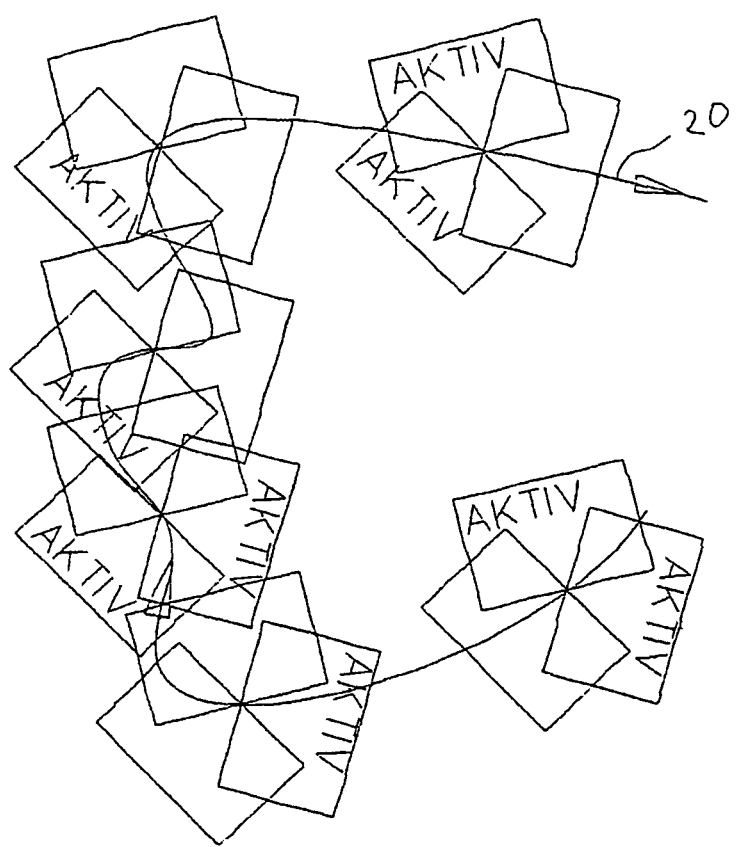
FIG. 4 illustrates another travel path of the apparatus according to the invention with regard to switching of a relevant camera.

FIG. 4 illustrates another progression of an adhesive trail 20, whereby a field of view is active (e.g., shown as "aktiv") 27. The camera 12, 13 and 14 having the corresponding active field of view is shown as an "aktiv" rectangle 27 while traveling along the adhesive trail 20.

Figure 5:
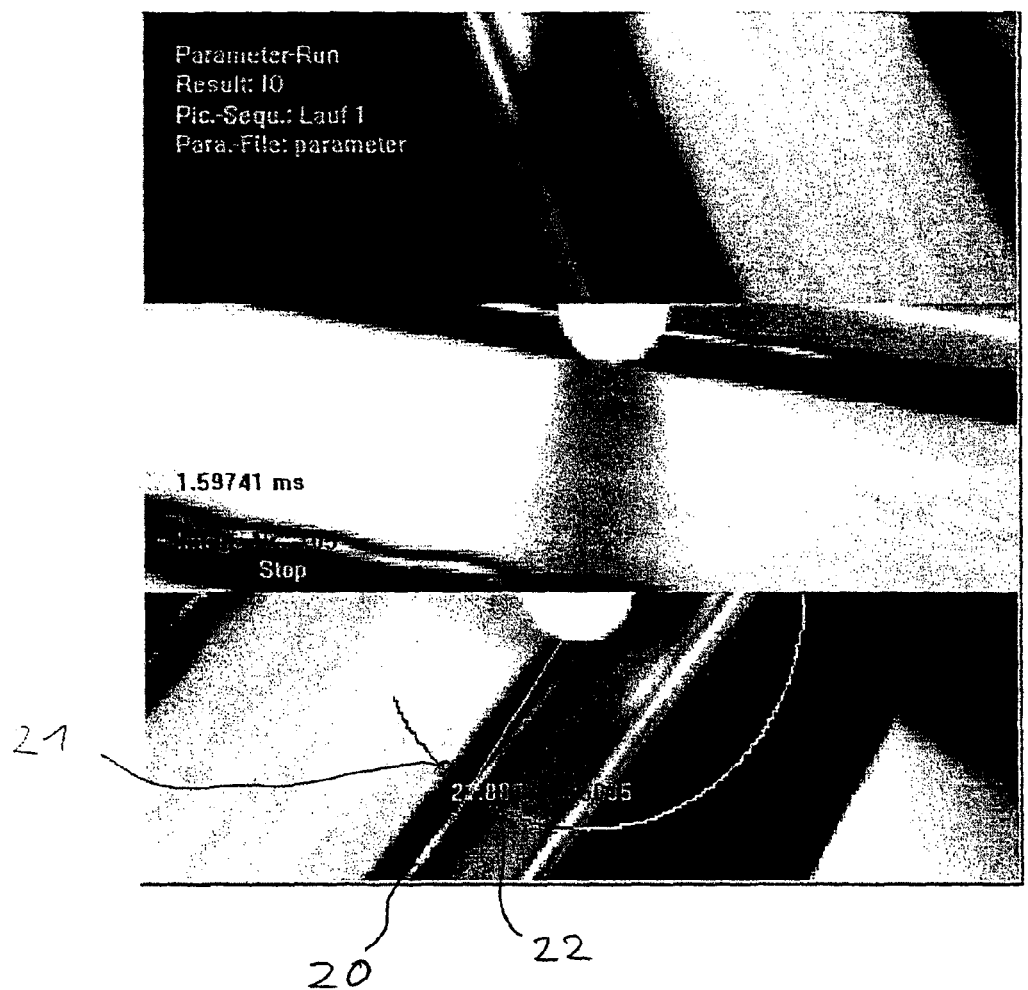
FIG. 5 is a view of a single image composed of three image strips from three cameras for online monitoring.

FIG. 5 illustrates three image strips 32, 33, and 34 that represent a relevant section or strip of an image of the three individual cameras 12, 13 and 14 (shown in FIG. 1). Each camera 12, 13 and 14 records a strip of the image in order to reduce the amount of data accordingly such that the recording rate can be increased. These individual image strips 32, 33, and 34 of the three cameras 12, 13 and 14 are then joined into an image. The image recording occurs at defined fixed time intervals and is independent of the robot control of the application facility 11. For example, the cameras 12, 13 and 14 only record a strip of the image having an image height of approximately 100 pixels (e.g., 100 image lines is used) instead of an image height of 450 pixels. By means of this partial scanning technique (i.e., partial reading-out of the image recording chip) only small data streams are generated such that the image recording rate can be increased severalfold. Therefore, the data analysis simultaneously captures the three image strips that are arranged one below the other of the individual cameras 12, 13 and 14 synchronously and in parallel and then joins them into a single image. As a result, the three image strips, are correctly arranged and assigned with regard to a location and a time relative to each other and without delay can be processed accordingly. The specific image recording technique facilitates simultaneous and parallel recording of individual camera 12, 13 and 14 that are stored as a sequence of images. Thus, the structure can be scanned once during the teach-in of a reference application structure.

Once the images of the three cameras 12, 13 and 14 are stored in a sequence of images, a parameterization of the reference track is carried out as the subsequent step of teaching-in the reference adhesive trail. A robot travel path, a robot travel time, a direction, a width, and a quality of the adhesive trail 20 are utilized to determine the parameterization. A type of vector chain for the adhesive trail 20 results, which allows a high image recording rate to be attained via comparably short partial sections (e.g., between 1 and 3 mm). Vectorization has another advantage, in that, the adhesive trail 20, being in the form of a vector chain, can be stored in a camera-transcending global coordinate system.

As shown in the bottom strip 34 of FIG. 5, a circular line is arranged around the center of the application facility 11, and two edge points 21 and 22 of the adhesive trail 20 are arranged on the circular line. The circular line is subdivided into a plurality of angles to provide overlapping areas of the individual cameras 12, 13 and 14 to facilitate a gapless coverage around the application facility 11. A range of angles from −10° to 130° is assigned to a first camera. A range of angles from 110° to 250° is assigned to a second camera, and a range of angles from 230° to −10° is assigned to a third camera. A global coordinant system results for the three image strips, which can be provided as either Cartesian coordinants or polar coordinants.

If the adhesive trail 20 progresses out of the field of view 23, 24 and 25 of a camera, the adhesive trail 20 is transiently in the overlapping area of the ranges of angles of the adjacent two cameras. If the adhesive trail 20 then progresses from the segment of the circular line of the one camera via the overlapping area to the segment of the circular line of another camera, an automatic switch is made from the one camera to the other camera. This is illustrated in FIG. 4 by means of the active fields of view 27 of the individual cameras 12, 13 and 14.

The individual cameras 12, 13 and 14 form a circular caliper whose center is formed by the application facility 11, whereby the search for the edges 21, 22 of the adhesive trail 20 proceeds on a circular line directly around the application facility 11. The individual cameras 12, 13 and 14 are essentially directed at the application facility 11 such that the axial longitudinal axes of the individual cameras 12, 13 and 14 intersect the longitudinal axis of the application facility 11.

A teach-in run or a teach-in of a reference adhesive trail is described in the following paragraphs.

The teach-in process of the reference adhesive trail can be started by a user by means of a mouse-click by selecting a track that indicates the position of the adhesive trail 20. This is sufficient for fully automatic recognition of position and direction of the adhesive trail 20 in the subsequent camera images because the image recording rate is sufficiently high and the individual images are recorded very shortly after one another (e.g., every 1 mm to 3 mm). From the starting point, the adhesive is scanned image by image, whereby the adhesive trail position and the adhesive trail angle detected in the current image are used as a priori knowledge for the upcoming image. The fact that the track radii usually exceed 20 mm facilitates fully automatic capture of the adhesive trail 20 without a human having to assess the image or the position of the adhesive trail 20. As a result, the search area can be limited which allows, by means of the high image recording rate, a determination of where the adhesive trail 20 will essentially progress to in the following image.

Figure 6:
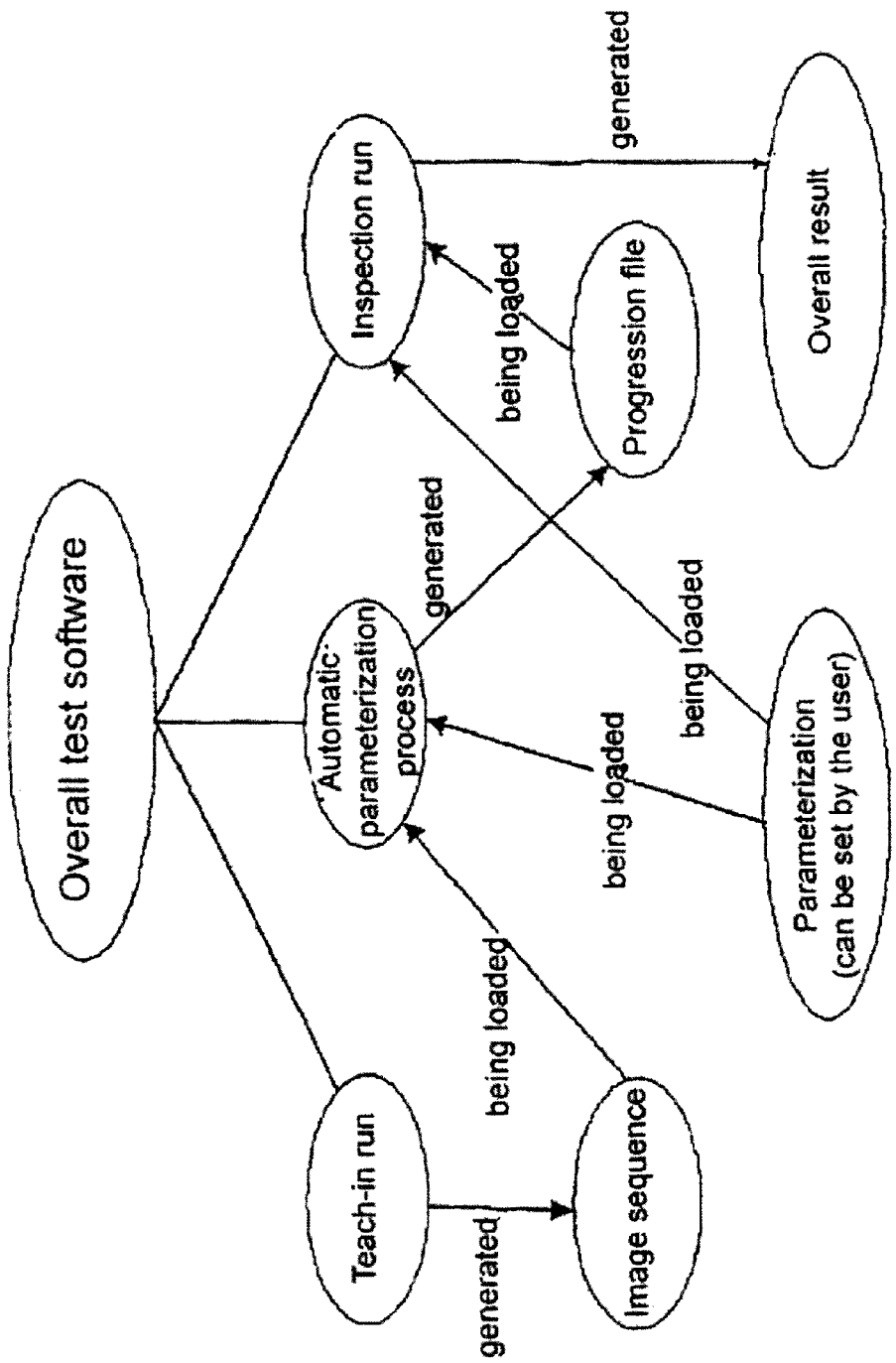
FIG. 6 illustrates the principles of the design of the software.

FIG. 6 illustrates the principles of the design of the software, whereby the teach-in run or teach-in run generates the image sequence. The image sequence, in turn, facilitates the automatic parameterization. This parameterization can be pre-set by the user, if applicable, and is used together with a progression file for inspection of an applied adhesive trail 20 during the inspection run.

The online monitoring of an applied adhesive trail 20 is described in the following paragraphs. The application facility 11 (shown in FIG. 1) applies the adhesive trail 20 onto the metal sheet 31, whereby the application facility 11 is moved together with cameras 12, 13 and 14 over the metal sheet 31. However, a kinematic inversion is also feasible, for instance the metal sheet 31 is moved and the application facility 11, including the cameras 12, 13 and 14, is arranged in a fixed position. The applied adhesive trail 20 is determined and analyzed synchronously and in parallel by the cameras 12, 13, 14. The cameras 12, 13, and 14 are on the circular line of the circular caliper (shown in FIG. 5), whereby each camera 12, 13, and 14 records only a strip of the image. The strips of images are joined into a single image that form a sequence of images. Thus, the image recording rate is increased in accordance with the data reduction attained by each camera 12, 13 and 14 recording only a strip of the image. The individual image strips in the joint image facilitate the synchronous and parallel as well as simultaneous capture of the three camera images. The individual images of the three cameras 12, 13 and 14 can be assigned directly as a function of location. As a result, online monitoring of the adhesive trail 20 is feasible in real-time and achieves high accuracy at high travel speeds due to the high image recording rate both in teaching-in a reference adhesive trail and in the inspection of the applied adhesive trail 20. The information concerning the adhesive trail 20 in the adhesive search area, the angle assignment of the sensor, the adhesive assessment, the robot travel path, and the robot travel time are summarized in a progression list.

According to an embodiment of the present invention, an assessment function (e.g., in particular a fuzzy assessment) can be used to find the edges of the adhesive trail 20. In order to determine and assess the adhesive trail 20, the following parameters described below are included in the calculation of a fuzzy assessment.

A width of a pair of edges (e.g., an edge 1: a left edge of the adhesive trail; an edge 2: a right edge of the adhesive trail), a mean gray scale value of the projected gray scale value profile between the pair of edges, an edge contrast (e.g., a geometric mean of amplitudes of the two edges), and a progression of position (e.g., directed deviation of a center between the two adhesive edges from a center of the search area, in pixels). By means of this plurality of parameters and the use of the fuzzy assessment function, the adhesive trail 20 can be automatically recognized in a reliable fashion and described very accurately.

The illumination module (not shown) for the apparatus according to the invention comprises light emitting diodes (LEDs), in particular infrared LEDs, ultra-violet LEDs (UV LEDs) or Red-Green-Blue LEDs (RGB LEDs). In order to attain a high contrast in an image recording, the LEDs can be flashed. For instance short, strong pulses of current on the order of 1.0 to 0.01 ms can be applied to the diodes. Thus, the light-emitting diodes are capable of emitting light of various colors. The advantage is that a sensor design can be switched to other types of adhesives or colors of adhesives without reconfiguration.

Figure 7:
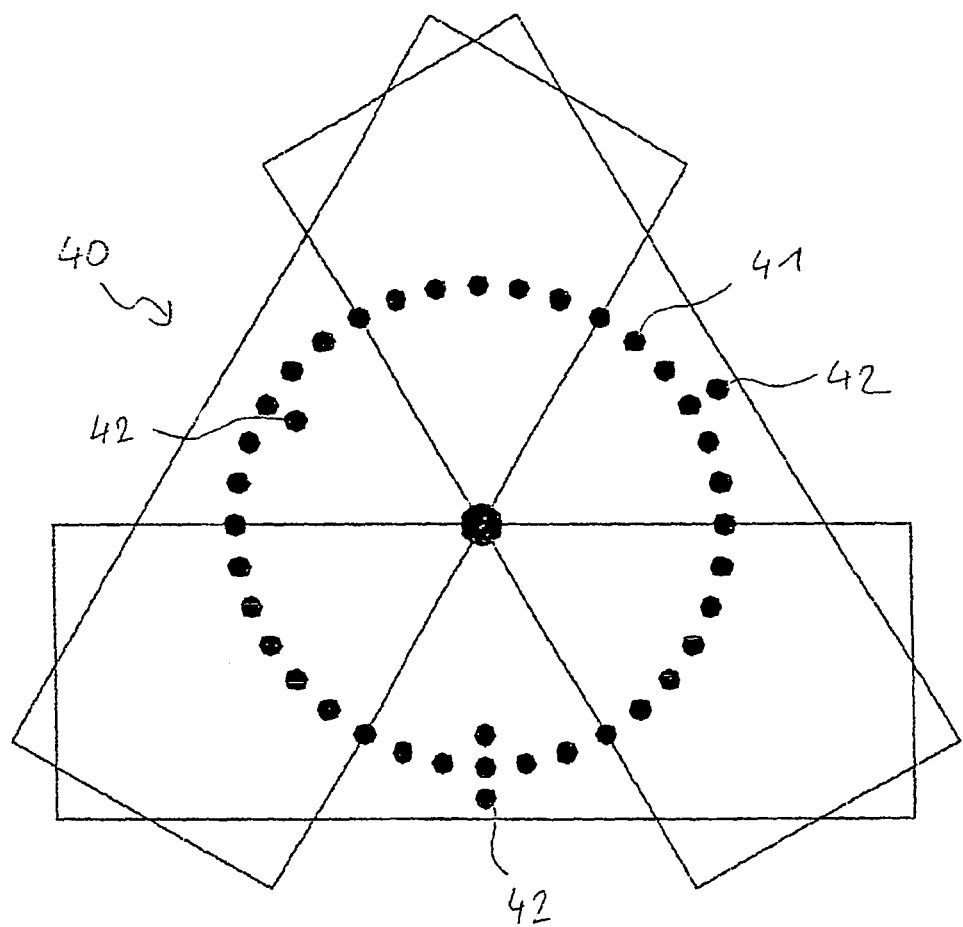
FIG. 7 illustrates a schematic view of a calibrating device according to the invention for calibrating individual cameras of an apparatus according to the invention for recognizing a structure to be applied onto a substrate.

FIG. 7 illustrates a calibration facility 40 in the form of a circular calibrating disc. The calibration facility 40 assigns the individual cameras 12, 13 and 14 a scaling factor, an angle assignment, and a center as well as a radius of a search circle. The calibrating disc consists of individual form elements 41 (e.g. shown as dots) that are arranged on a circular line at an angle distance of approximately 10° Moreover, marker sites 42 are arranged at an equal distance from each other in order to calibrate three cameras 12, 13 and 14. A compensation calculation is used to calculate from the coordinates of the centers of the individual dots, on the one hand, the scaling factors of the individual cameras 12, 13 and 14 and, on the other hand, the center as well as the radius of the search area. The marker sites at angles of 0°, 120°, and 240° in the global coordinate system allow the angle assignment and the corresponding fields of view of the individual cameras 12, 13 and 14 to be determined. The field of view of the individual cameras 12, 13 and 14 is indicated, in particular, by the three rectangles 43, 44, and 45 (shown in FIG. 7). The form elements 41 can correspond to the circular line of the circular caliper for detection of the adhesive trail 20.

Figure 8:
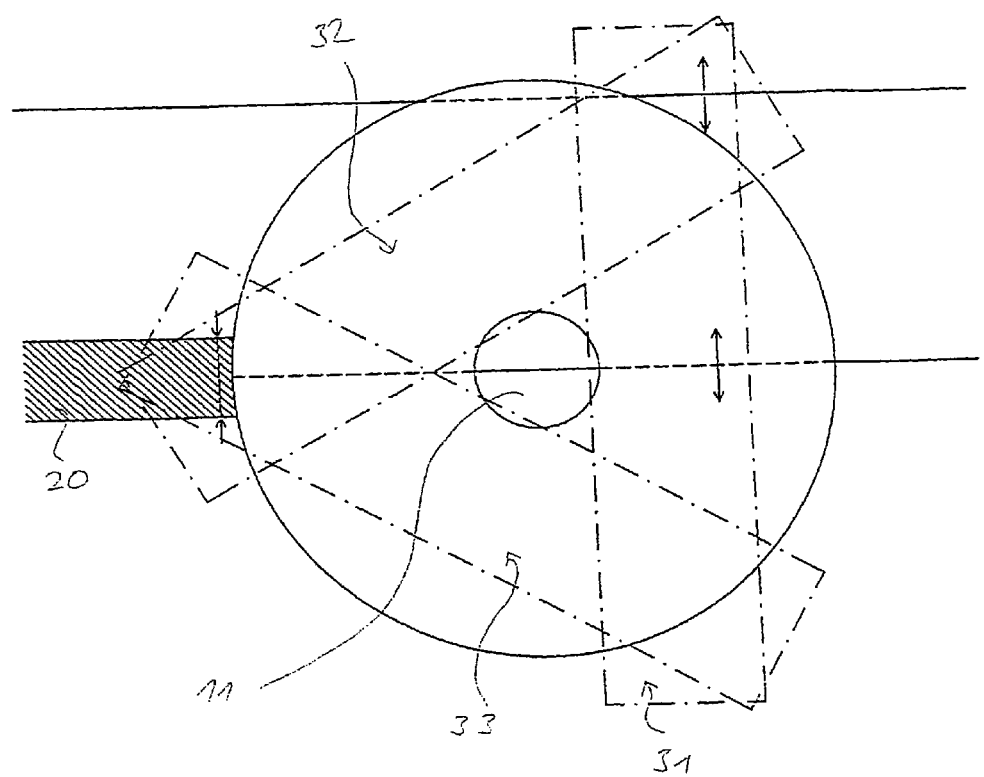
FIG. 8 illustrates a top view onto a substrate with an adhesive trail applied with regard to monitoring the application.

FIG. 8 illustrates the application facility 11, whereby the strips 31, 32, and 33 around the application facility 11 each are shown by dashed lines that represent the read-out area of the individual cameras 12, 13 and 14. Two active cameras monitor the adhesive trail 20, such that the adhesive trail 20 is monitored in the overlapping area of the strips 32 and 33. If the progression of the adhesive trail 20 relative to the application facility 11 changes, only one of the cameras 12, 13 and 14 becomes active, and an essentially circular caliper (not shown) that is arranged to be concentric around the application facility 11 is used.

According to this embodiment, the circular caliper is formed by multiple cameras 12, 13 and 14 that are arranged around the application facility 11, but, in particular, can be attached at a different radius from the center of the application facility 11. For an inspection of an application structure or adhesive trail 20, the cameras 12, 13 and 14 are directed at a circle or circular line whose center coincides with the center of the application facility 11. The optical detection of the adhesive trail 20 then proceeds on this circular line.

Figure 9:
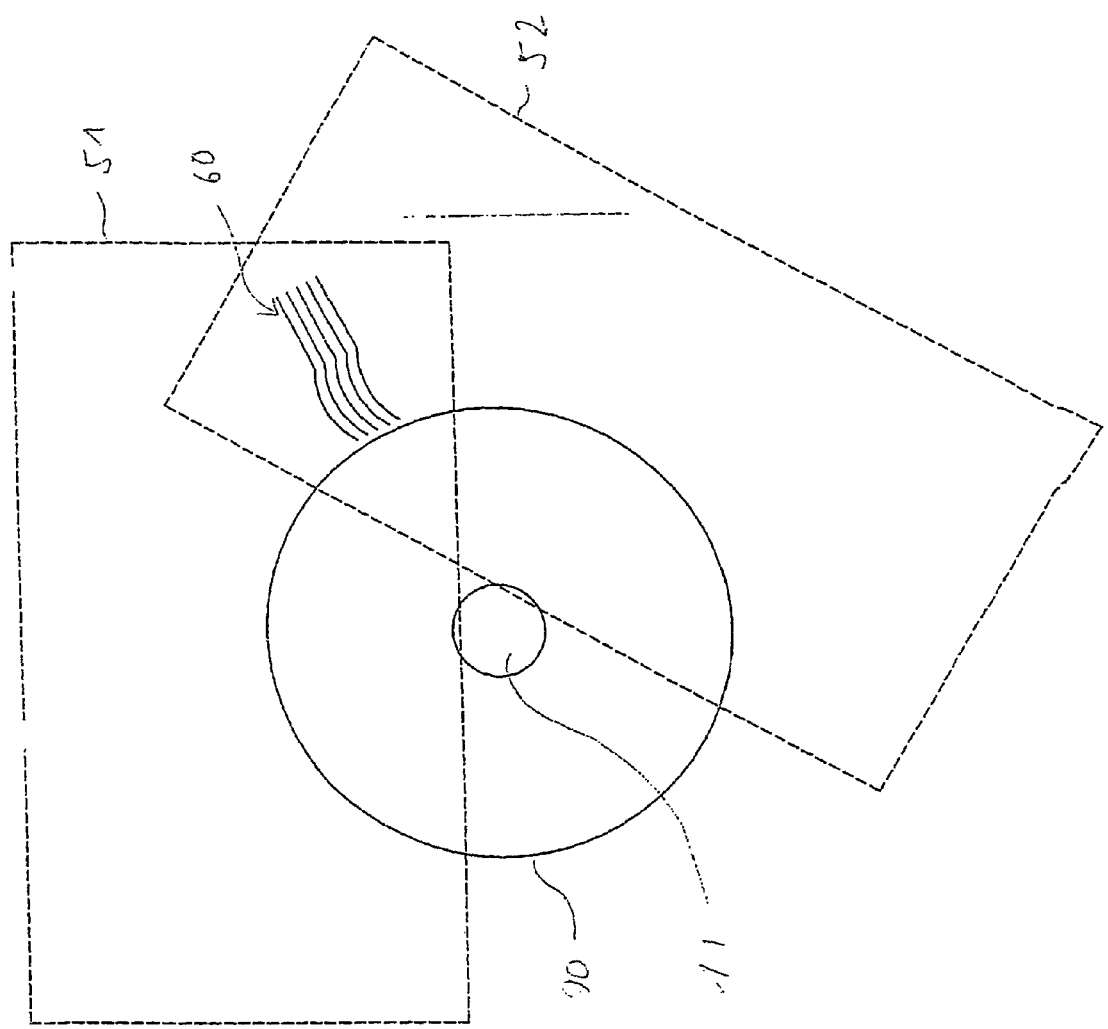
FIG. 9 illustrates a top view with regard to analysis of the profile.

FIG. 9 illustrates a three-dimensional profile analysis by means of a projection to provide for a positional correction of the application facility 11. For reasons of clarity of presentation, FIG. 9 illustrates two camera fields of view 51, 52 indicated by the dashed lines. In the overlapping area of the two camera fields of view 51, 52 are shown a plurality of laser lines 60 that are used for profile analysis with regard to the width and contour of structure lines. The laser lines are also used for generation of soft contours. The laser lines 60 are generated by a projection facility that can, for example, be arranged on the optical sensor with three cameras 12, 13 and 14. Moreover, the projection facility can also be arranged directly on the application facility 11. The sensor with the three cameras 12, 13 and 14 is shown schematically by the circle 70. The laser lines 60 or laser strips projected onto the component 30 or metal sheet 31 highlight contours on the component that cannot be used for three-dimensional analysis by conventional image processing. Artificial features are generated by means of the laser lines 60 on the component and can subsequently be analyzed by means of image processing utilizing stereometry. Thus, FIG. 9 illustrates the principle of three-dimensional positional recognition prior to the application of a sealing agent where no hard, analyzable features are present.

What is claimed:

1. A method for recognizing a structure to be applied onto a substrate, the method comprising:
   acquiring, by means of a single scan of a reference application structure using multiple cameras, a teach-in of the reference application structure; and
   storing a sequence of images of the reference application structure;
   wherein each of the cameras records each corresponding image as an image strip that forms part of the sequence of images, and wherein image recording rate is increased in line with a data reduction achieved by recording each image as an image strip.

2. A method for recognizing a structure to be applied onto a substrate, the method comprising:
   acquiring, by means of a single scan of a reference application structure using multiple cameras, a teach-in of the reference application structure; and
   storing a sequence of images of the reference application structure;
   wherein each of the cameras records each corresponding image as an image strip that forms part of the sequence of images, and wherein for each camera, approximately one quarter of associated image lines are used for each corresponding image strip.

3. A method for recognizing a structure to be applied onto a substrate, the method comprising:
   acquiring, by means of a single scan of a reference application structure using multiple cameras, a teach-in of the reference application structure;
   storing a sequence of images of the reference application structure, wherein each of the cameras records each corresponding image as an image strip that forms part of the sequence of images; and
   applying the structure to the substrate as an adhesive trail, wherein an edge of the adhesive trail is determined on a surrounding track that is approximately a circular line, and wherein the adhesive trail is applied such that the adhesive trail progresses within the surrounding track.

4. The method according to claim 1, further comprising applying the structure onto the substrate and processing a scan of the applied structure as an optical representation.

5. The method according to claim 1, further comprising joining the sequence of images into a single image.

6. The method according to claim 1, wherein for each camera, approximately one quarter of associated image lines are used for each corresponding image strip.

7. The method according to claim 1, further comprising:
   parameterizing the sequence of images by means of a one-time external marking of the reference application structure.

8. The method according to claim 7, wherein the parameterization comprises a robot travel path, a robot travel time, a direction, a width and a quality of an adhesive trail.

9. The method according to claim 1 further comprising applying the structure to the substrate as an adhesive trail, and analyzing the adhesive trail utilizing an assessment function, wherein the assessment function comprises a fuzzy assessment.

10. The method according to claim 9, wherein a calculation by means of the assessment function is determined by at least one of a width of a pair of edges comprising a right edge and a left edge of the adhesive trail, a mean gray scale value of a projected gray scale value profile between the pair of edges, an edge contrast, and a position of the progression of the adhesive trail.

11. The method according to claim 1 further comprising applying the structure to the substrate as an adhesive trail, wherein an edge of the adhesive trail is determined on a surrounding track that is approximately a circular line, and wherein the adhesive trail is applied such that the adhesive trail progresses within the surrounding track.

12. The method according to claim 3 wherein a center of the circular line approximately coincides with a site from which an adhesive emanates to form the adhesive trail.

13. The method according to claim 3 wherein each camera monitors at least a segment of at least one of the circular line and an orbit formed by the circular line.

14. The method according to claim 1, wherein each camera monitors at least one overlapping area with at least one adjacent camera.

15. The method according to claim 3 wherein a segment of the circular line is assigned to the images of a respective camera, and wherein the angle values of the circular line range from 0° to 360° and comprise a global coordinate system.

16. The method according to claim 15, wherein the multiple cameras include first, second and third cameras, wherein the first camera covers at least a range of angles between −10° to 130°, the second camera covers at least a range of angles between 110° to 250°, and the third camera covers at least a range of angles between 230° to 10°.

17. The method according to claim 13 further comprising automatically switching from one camera to another camera when the adhesive trail progresses from the segment of the circular line of the one camera via an overlapping area to the segment of the circular line of the another camera.

18. The method according to claim 1 further comprising utilizing a plurality of light emitting diodes (LEDs) to illuminate the structure with a color that is a suitable contrast to the color of the structure.

19. The method according to claim 18, wherein the LEDs comprise infrared LEDs, ultra-violet (UV) LEDs and/or Red-Green-Blue (RGB) LEDs.

20. The method according to claim 1 further comprising determining a reference contour utilizing at least two cameras to perform a three-dimensional positional correction for an application facility by means of a stereometry procedure.

21. The method according to claim 20, wherein the at least two cameras each record an image comprising at least one of a full image and a large image of at least one of the substrate, a section of a component, and a plurality of components.

22. The method according to claim 21, wherein the full images or the large images of the at least two cameras comprise an overlapping area in a leading direction.

23. The method according to claim 20 further comprising adjusting the application facility prior to applying the structure by utilizing a three-dimensional recognition of the reference contour position.

24. The method according to claim 20 further comprising applying a plurality of laser lines to the substrate to form a projection onto the area of the reference contour for a three-dimensional analysis.

25. The method according to claim 1 further comprising utilizing a calibrating device having marker points located at 0°, 120°, and 240° of a circular arc to calibrate the cameras, wherein the individual cameras are calibrated in order to assign an angle assignment.

26. The method according to claim 1 further comprising applying the structure onto the substrate using an application facility, and measuring a distance from the application facility to a component to perform a positional test of the applied structure.

27. The method according to claim 18 further comprising flashing the LEDs by applying pulses of current ranging in duration from 1.0 to 0.01 ms to the LEDs.

28. The method according to claim 26 wherein a line-shaped gray scale value scan is used for distance measurement.

* * * * *